(12) United States Patent
Hultgren

(10) Patent No.: US 6,200,135 B1
(45) Date of Patent: Mar. 13, 2001

(54) SCANNING APPARATUS FIXTURE FOR HOLDING IMPRESSION TRAYS

(75) Inventor: Bruce Willard Hultgren, Victoria, MN (US)

(73) Assignee: Iris Development Corporation, Eden Prairie, MN (US)

(*) Notice: Subject to any disclaimer, the term of this patent is extended or adjusted under 35 U.S.C. 154(b) by 0 days.

(21) Appl. No.: 09/312,417

(22) Filed: May 14, 1999

Related U.S. Application Data

(63) Continuation-in-part of application No. 08/789,918, filed on Jan. 28, 1997, now abandoned.

(51) Int. Cl.$^7$ ............................................ A61C 1/14

(52) U.S. Cl. ................................. 433/49; 433/72

(58) Field of Search .................. 433/49, 72, 29, 433/53, 215

(56) References Cited

U.S. PATENT DOCUMENTS

| | | | |
|---|---|---|---|
| 849,758 | * | 4/1907 | Titus . |
| 1,244,792 | * | 10/1917 | Stoll . |
| 4,182,312 | * | 1/1980 | Mushabac . |
| 4,196,519 | * | 4/1980 | Ouaknine ........................... 433/49 |
| 4,449,927 | * | 5/1984 | Taylor et al. . |
| 4,573,917 | * | 3/1986 | Erickson ........................... 433/75 |
| 4,602,905 | * | 7/1986 | O'Keefe, III . |
| 4,611,288 | * | 9/1986 | Duret et al. . |
| 4,722,686 | * | 2/1988 | Salib .................................. 433/72 |
| 4,752,964 | * | 6/1988 | Okada et al. . |
| 4,827,909 | * | 5/1989 | Kato et al. . |
| 4,935,635 | * | 6/1990 | O'Harra . |
| 5,017,139 | * | 5/1991 | Mushabac . |
| 5,027,281 | * | 6/1991 | Rekow et al. . |
| 5,071,252 | * | 12/1991 | Matsuura . |
| 5,078,599 | * | 1/1992 | Eenboom et al. .................. 433/215 |
| 5,102,335 | * | 4/1992 | Getz . |
| 5,121,333 | * | 6/1992 | Riley et al. . |
| 5,121,334 | * | 6/1992 | Riley et al. . |
| 5,124,524 | * | 6/1992 | Schuster et al. . |
| 5,128,870 | * | 7/1992 | Erdman et al. . |
| 5,173,048 | * | 12/1992 | Summer . |
| 5,184,306 | * | 2/1993 | Erdman et al. . |
| 5,198,877 | * | 3/1993 | Schulz . |

(List continued on next page.)

FOREIGN PATENT DOCUMENTS

WO 91/02458   10/1991   (WO) .

OTHER PUBLICATIONS

"Digital Record Keeping", http://www.webworldinc.com/orthovision/RecordsBrochure.htm (Jul. 31, 1996).
"Ortho–Vision Technologies", http://www.webwordinc.com/orthovision.News1Q96.htm (Jul. 31, 1996).
"OTP for Windows", http://www.webworldinc.com/orthovision/OTPBrochure.htm (Jul. 31, 1996).
"Treat Your Patients With Care", http://www.sibworldinc.com/orthovision/treatwithcare.htm (Jul. 31, 1996).
"Welcome to Ortho–Vision", http://www.webworldinc.com/orthovision/ (Jul. 31, 1996).

Primary Examiner—Ralph A. Lewis
(74) Attorney, Agent, or Firm—Merchant & Gould P.C.

(57) ABSTRACT

The present invention provides a fixture or tooling for securely holding an impression tray or study cast on a stage of an X-Y-Z scanning machine to permit accurate scanning of the impression tray, or the study cast, by the scanner of the scanning machine. In one embodiment, the fixture includes a pivoting clamp member that clamps a handle member on the tray or study cast. In a second embodiment, the fixture includes a block slidably disposed thereon for clamping an impression tray or a study cast in a clamping section. A registration fixture utilizing a pair of locking fixtures to simultaneously hold the study casts of the upper and lower sets of teeth to permit registration of the study casts is also provided.

13 Claims, 14 Drawing Sheets

U.S. PATENT DOCUMENTS

| | | | |
|---|---|---|---|
| 5,224,049 | * | 6/1993 | Mushabac . |
| 5,257,184 | * | 10/1993 | Mushabac . |
| 5,257,203 | * | 10/1993 | Riley et al. . |
| 5,273,429 | * | 12/1993 | Rekow et al. . |
| 5,338,198 | * | 8/1994 | Wu et al. . |
| 5,343,391 | * | 8/1994 | Mushabac . |
| 5,346,395 | * | 9/1994 | Adell . |
| 5,347,454 | * | 9/1994 | Mushabac . |
| 5,348,474 | * | 9/1994 | Pasini . |
| 5,432,703 | * | 7/1995 | Clynch et al. . |
| 5,448,472 | * | 9/1995 | Mushabac . |
| 5,452,219 | | 9/1995 | Dehoff et al. . |
| 5,549,476 | | 8/1996 | Stern . |
| 5,551,873 | * | 9/1996 | Aiba ................................ 433/72 |
| 5,846,081 | * | 12/1998 | Bushway .......................... 433/215 |

\* cited by examiner

SCANNING APPARATUS FIXTURE FOR HOLDING IMPRESSION TRAYS

CROSS REFERENCE TO RELATED APPLICATIONS

This is a continuation-in-part of application Ser. No. 08/789,918, filed on Jan. 28, 1997, now abandoned. This application further relates to copending application Ser. No. 09/311,436 titled "Buccal Impression Registration Apparatus, and Method of Use", filed on May 14, 2000, and commonly owned by the Assignee of the present invention.

FIELD OF THE INVENTION

The present invention relates generally to a system of dental modeling and imaging which creates digital images of teeth topography; and more particularly relates to a fixture for securely holding a dental member, such as a dental impression tray or study cast, on a table of a scanning machine to permit scanning by a scanner.

BACKGROUND OF THE INVENTION

Dental study casts are an integral part of a dentist's understanding of how a patient's teeth and bite function in a static relationship. This static relationship serves three important functions. The primary function is one of a diagnostic function for interpretation of any discrepancies or problems that exist within the bite relationship. The second function is educational. For example, the study casts provide better communication as a concrete model while helping the patient understand any discrepancies that may exist in the way their teeth function in that static relationship. Third, the dental study casts serve an important medical/legal function in defining the pre-existing static bite relationship prior to the performance of any work. This work can be defined either from an oral surgical standpoint, prosthetic standpoint or orthodontic/periodontal standpoint.

Significant complications are associated with study casts, however, since the casts need to be stored for an extended period (generally seven years). For example, the storage of the study casts requires large amounts of space in humidity controlled environments, as well as extensive laboratory procedures involving OSHA guidelines and space utilization for the study casts to be constructed. In addition, a significant amount of turn-around time is required for the curing process of the plastic study casts to occur. In light of these significant constraints as well as the importance associated with having an accurate recording of the pre-existing bite relationship, there arises a need for an apparatus (or system) and method in which electronic image data can be collected from an impression to circumvent the need for storage of physical study casts.

Prior to discussing a summary of the present invention, however, detailed discussions of the construction of a working model (study cast) of the teeth and other prior art devices will be presented.

As noted above, in order to study dental work to be performed on a patient's teeth, a working model of the teeth constructed of a plaster study cast is created. The plaster cast is based on a series of impressions taken to obtain the geometry of the teeth. To take an impression, alginate impression material is poured into a tray (i.e., an impression tray) which is then introduced into the patient's mouth for a period of time (typically one to two minutes). The impression material sets about the teeth and soft tissues forming a negative impression. The patient also bites into a soft material for registering a simultaneous imprint of the upper and lower teeth which records the relationship of the teeth in the upper and lower jaws respectively in three planes of space.

Once the impressions have set, they are sent to a lab to be processed into an upper and lower plaster study cast. The study casts are articulated together via the bite registration material to reproduce the bite of the patient. After construction, the study casts are returned to the dentist/orthodontist as a working study cast.

A serious drawback of this method is the number of labor intensive steps required to produce the study casts, the space and legal storage requirements of the study casts, and the inability to interface the study casts interactively with other diagnosis information (e.g., photographs and radiographs). Accordingly, if additional work is required, the cast fails in some way or is damaged, and/or the cast is lost, then an additional impression series must be taken. Therefore, there also exists a need in the art to develop a set of electronic data from the series of dental impressions wherein only a single impression need be taken for multiple interactive functions.

In the past, several devices have been designed for the electronic imaging of teeth. Also, other devices are known which utilize numerical data to create prototype devices. While known examples of such systems and devices follow, generally such systems do not provide the accuracy required for orthodontic work. Instead, such systems are generally useful only for crowns, fillings, etc.

U.S. Pat. No. 4,182,312 generally discloses a dental probe having a stylus which is commented through a rod to a three position transducer. Three signals are produced for indicating the position of the probe at any point to which the probe is applied. The transducers are mounted on an index tray which is adapted to be fastened to the jaw of the patient. Thus the patient's jaw becomes the origin against which all measurements are made. Contact between the tip of the stylus and the patient's tissue completes a circuit to turn on a recording mechanism which receives the transducer's outputs.

U.S. Pat. No. 4,611,288 generally discloses a method of producing dental prostheses (e.g., crowns, inlays, dentures and the like) using an optical impression taken of the oral region with nontraumatic radiation. The reflected waves are transformed into numerical data which is used to operate a numerically controlled machine in the fabrication process.

U.S. Pat. No. 4,752,964 generally discloses an apparatus for producing, from an object having a three-dimensional shape, a shape equivalent or analogous to the three-dimensional shape. Here, light is irradiated to the object in an optical cutting plane. The light is picked up by an image pick-up device, and two-dimensional positions of the light are obtained in a direction perpendicular to the optical cutting plane to determine its three dimensional shape.

U.S. Pat. No. 4,935,635 generally discloses a three-dimensional point measuring system which includes a laser diode for projecting a triangulating beam at a surface to be mapped, with the beam scanned repeatedly across the surface. Photodetectors detect the position of the beam as reflected from the mapped surface, given by triangulation Z-axis or depth information. Correlation of a particular point with the position of the scanner along the scan line gives Y-axis information, or information in a width direction. The scanner and diode are mounted on a slide or platform device which moves perpendicularly to the Y axis in the direction in an out of the mouth, driven by a stepper motor, and the monitored position of the stepper motor is coordinated with the other information on each spot to yield X-axis information.

U.S. Pat. No. 5,198,877 generally discloses a method and apparatus for optically sampling numerous points on the surface of an object to remotely sense its shape utilizing two stages. The first stage employs a moveable non-contact scanner, which in normal operation sweeps a narrow beam of light across the object, illuminating a single point of the object at any given instant in time. The location of that point relative to the scanner is sensed by multiple linear photo-detector arrays behind lenses in the scanner. These sense the location by measuring the relative angular parallax of the point. The second stage employs multiple fixed but widely separated photoelectronic sensors, to detect the locations of several light sources affixed to the scanner. Individual light sources are distinguished by time-multiplexing their on-off states. A coordinate computer calculates the absolute spatial positions where the scanner light beam is incident on the object to generate a computer model.

U.S. Pat. No. 5,224,049 discloses a method for use in preparing a dental prosthesis and U.S. Pat. No. 5,347,454 generally discloses a system for use in preparing a dental prosthesis.

U.S. Pat. No. 5,448,472 discloses a method for collecting three-dimensional surface information in dental applications via a video camera. A tape strip is applied to a tooth surface to provide a distance reference or standard for use by a computer in analyzing the video data to determine actual distances. The tape strips are additionally provided with identification markings identifying the type of surfaces and the teeth to which the tape strips are attached.

Each of the foregoing systems, devices and methods suffer the drawback in that bulky, expensive specialized devices are required. The processes are extremely time consuming or require the introduction of devices into the patient's mouth for extended periods of time or which leads to patient discomfort. Also, these systems are limited to dental restorative procedures only. Reduced accuracy and precision of the measurements also greatly limit the usefulness of these systems to direct scanning of the dental impressions, study casts or both.

Therefore, there arises a need for an easy to use apparatus that is able to securely hold an impression tray on a stage or table of a scanning machine to permit accurate scanning of an impression formed on the impression tray.

SUMMARY OF THE INVENTION

The present invention provides a fixture or tooling for securely holding an impression tray or study cast on a table of an X-Y-Z scanning machine to permit accurate scanning of the negative impression on the impression tray, or the study cast, by the scanner of the scanning machine. In this manner, a set of electronic data related to the patient's teeth and surrounding soft tissues can be generated, which can then be used for a number of purposes including visual display of the arrangement of the patient's teeth, storage of a patient base-line, creation of one or more study casts, and transmission to a remote location for analysis, among others.

In a preferred embodiment of the fixture according to the principles of the present invention, the fixture includes a base member that is adapted so as to be mountable onto the stage of the scanning machine, and a locking fixture detachably connected to the base member. The locking fixture includes a body portion and a clamp means disposed on the body portion for clamping a dental member onto the body portion. The locking fixture thus securely holds the dental member in a stationary manner to enable accurate scanning of the dental member by the scanner of the scanning machine.

The dental member may be defined as an impression tray or a study cast. In a first embodiment, when the tray or cast includes an elongate handle connected thereto, the body portion of the fixture includes a groove formed therein and the clamp means comprises a spring biased lever pivotally attached to the body portion. The elongate handle is disposed within the groove and clamped therein by the pivoting lever to securely fix the impression tray or study cast to enable accurate scanning by the scanner of the scanning machine.

In a second embodiment of the fixture according to the principles of the present invention, the fixture is constructed so as to hold a study cast or a dental impression tray without an elongate handle connected thereto. In this instance, the clamp means includes a pair of clamp blocks connected to the body portion, and a slide block slidably mounted on the body portion. The clamp blocks and slide block define a clamp section therebetween that receives the impression tray or study cast. The slide block is then slid into contact with the impression tray or study cast and subsequently locked in place to thereby securely fix the impression tray or study cast in the clamp section to enable accurate scanning by the scanner of the scanning machine.

In yet another aspect of the invention, a registration fixture is provided for simultaneously holding study casts of the upper and lower sets of teeth to enable registration of the two study casts. The registration fixture includes a support base having a first locking fixture secured thereto. The first locking fixture includes a first clamp mechanism that is configured to clamp a study cast of an upper or lower set of teeth. A pair of guide rods are oriented substantially parallel to each other, with each guide rod including a first end secured to the first locking fixture and a second, distal end spaced from the first locking fixture. A second locking fixture is slidably supported on the guide rods for sliding movement towards and away from the first locking fixture, with the second locking fixture including a second clamp mechanism configured to clamp a study cast of an upper or lower set of teeth. In this manner, the study cast of either the upper or lower set of teeth can be secured on the first or second locking fixture, while the other study cast of the upper or lower set of teeth is secured on other locking fixture. The second locking fixture is then slid toward the first locking fixture so as to bring the two study casts into registration. In a more preferred embodiment, the second locking fixture is independently adjustable, relative to the first locking fixture, so as to permit precise registration of the two study casts.

Therefore it is an object of the present invention to provide a fixture or tooling for securely holding a dental member, such as an impression tray or a study cast, on a stage of a scanning machine to facilitate accurate scanning of the dental member by the scanner. The set of electronic data generated by the scanning can then be electronically stored and manipulated for a variety of uses.

It is a further object of the invention to provide a registration fixture for securely holding study casts of the upper and lower sets of teeth, so as to permit the study casts to be brought into precise registration with each other to reflect the bite registration of the patient.

These and other advantages and features which characterize the present invention are pointed out with particularity in the claims annexed hereto and forming a further part hereto. However, for a better understanding of the invention, reference should be had to the following drawing and detailed description.

BRIEF DESCRIPTION OF THE DRAWINGS

Referring to the drawing, wherein like numerals represent like parts throughout the several views.

DETAILED DESCRIPTION OF THE PREFERRED EMBODIMENT

Figure 1:
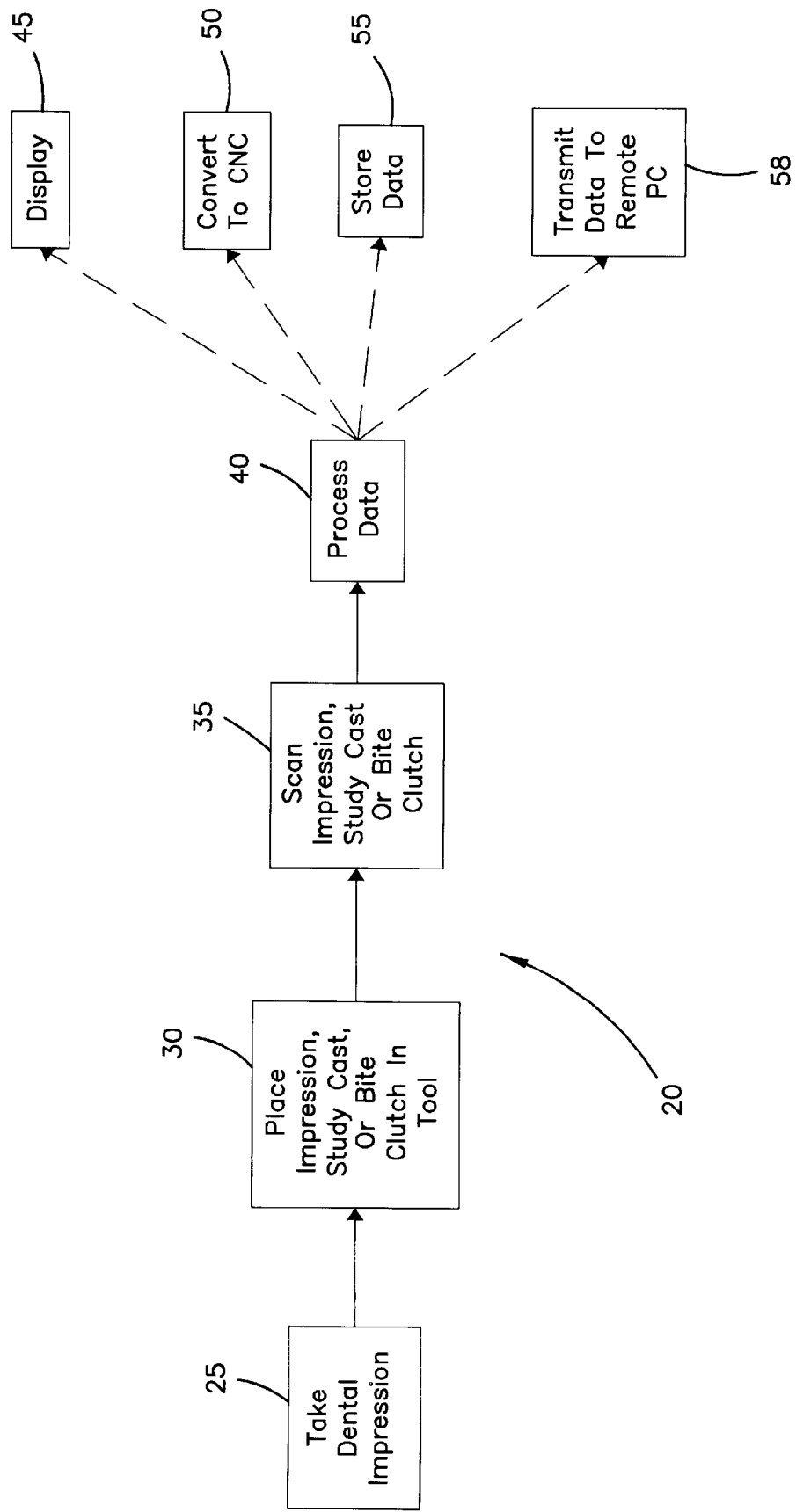
FIG. 1 illustrates the method steps 20 used to practice the principles of the present invention.
Figure 2A:
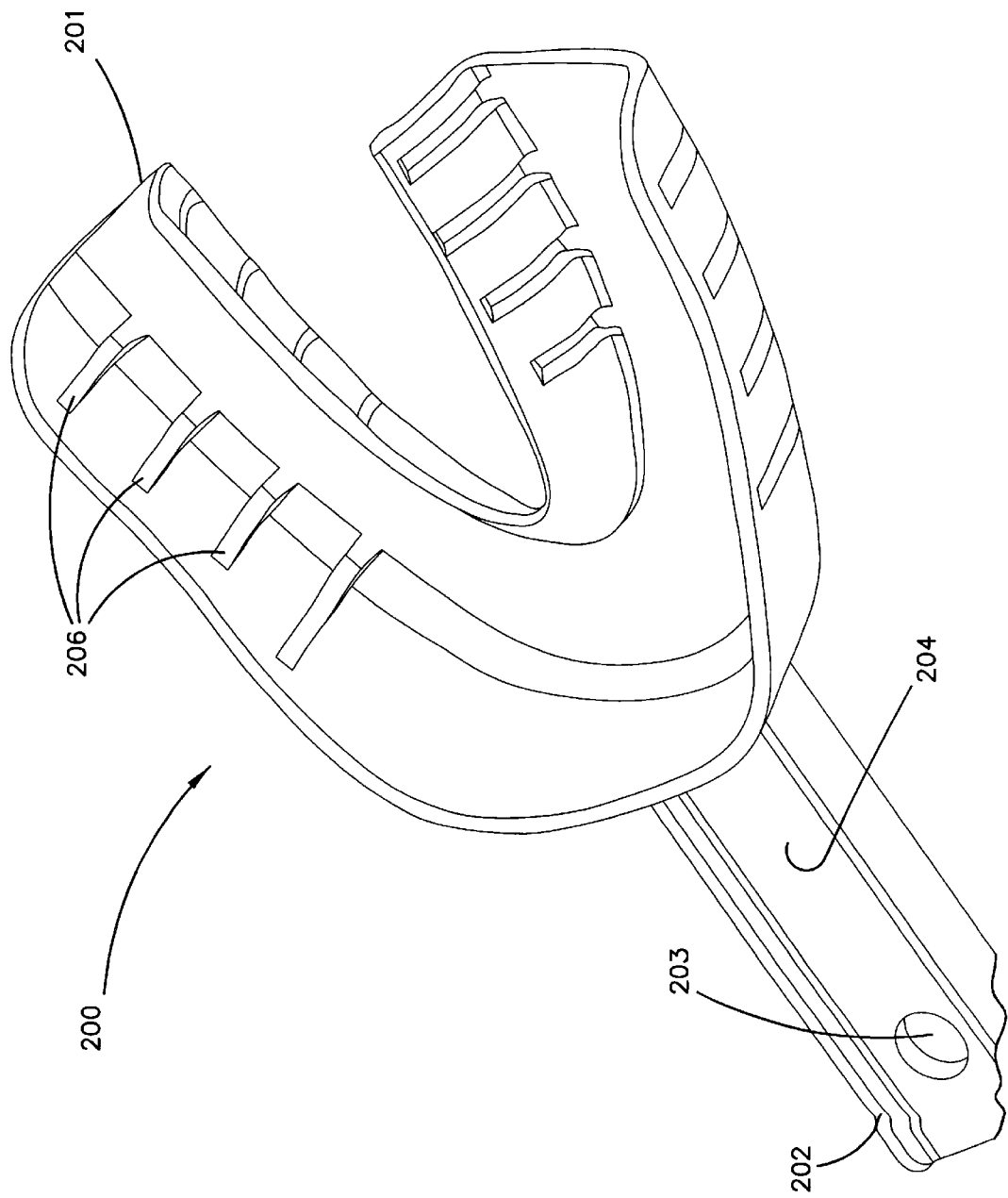
FIGS. 2a and 2b illustrate perspective views of lower 200 and upper 220 impression trays, respectively, used in connection with the present invention.
Figure 2B:
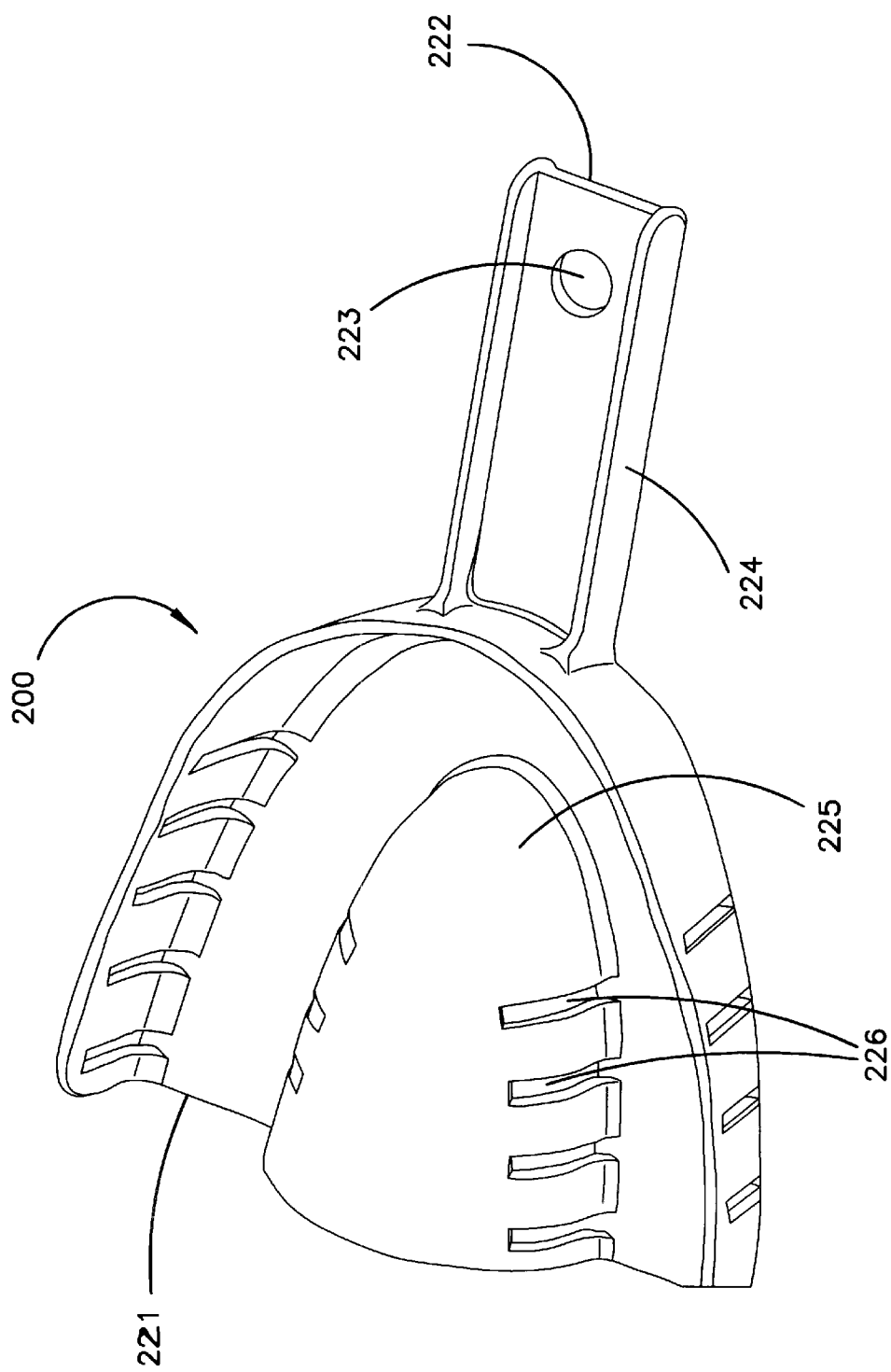
Figure 3A:
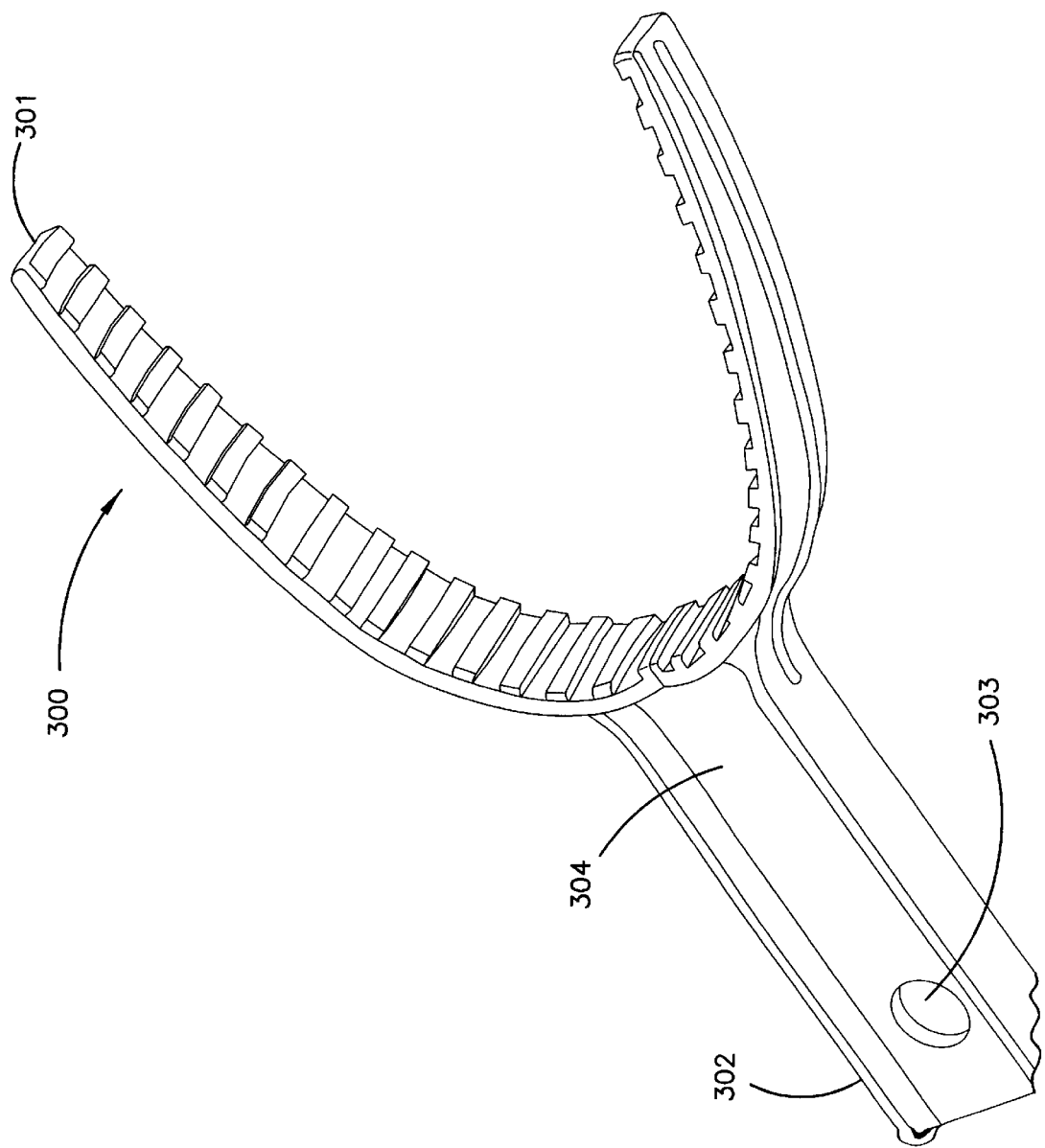
FIG. 3a illustrates a perspective view of a registration tray 300 used in connection with the present invention.
Figure 3B:
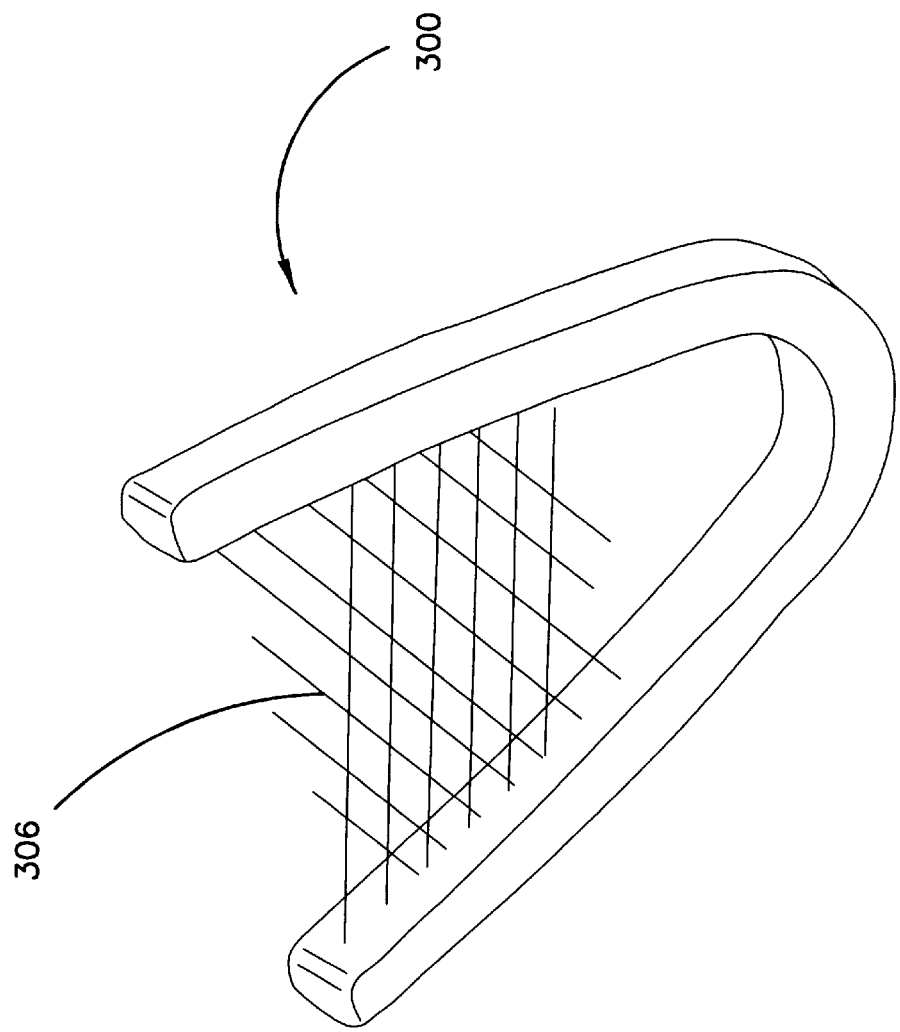
FIG. 3b diagrammatically illustrates the preferred arrangement and configuration of the impression material retaining mesh 306 used in connection with tray 300.

Referring first to FIG. 1, the overall method used with the present invention is illustrated generally by the designation 20. First, at block 25, a dental impression of a patient's teeth and surrounding soft tissues (hereafter referred to collectively as "teeth" for convenience) is taken. The impression material hardens, forming a negative image of the teeth. The lower 200 and upper 220 trays used in connection with taking the impression are described below and are best seen in FIGS. 2a and 2b respectively. The bite/clutch tray 300 used in connection with determining the correct spatial orientation and relationship between the upper and lower impressions is described below and is best seen in FIGS. 3a and 3b.

At block 30, the impression tray 200 or 220 is placed in the tool or fixture 600 (described below and best seen in FIGS. 5 and 7–17). The fixture 600 is used to securely hold the tray 200, 220, and/or 300 during the scanning step. The fixture 600 may also aid the scanning step by helping rotate the mold so that the image data can be properly generated. It will be appreciated that during this step at least one of the trays 200 and 220 include the hardened impression material which defines a negative image impression or mold of a patient's teeth.

Next at block 35, the scan of the impression occurs. In the preferred embodiment, a scanner manufactured by Laser Design Inc. of Minneapolis, Minn. designated as model number 8849648 may be used. The operation and scanning methodology used by this type of scanner is generally described in U.S. Pat. No. 5,124,524 (which is hereby incorporated herein by reference). Generally, this type of scanner is referred to as a line scanner device. It will be appreciated that for a complete study cast of the upper and lower teeth, two scans of the negative image impressions occur (i.e., one lower and one upper). Further, in order to properly reference the two sets of teeth together, a scan of the bite tray 300 impression also takes place.

Figure 6:
FIG. 6 is a perspective view of a positive image of a scanned portion of a study cast.

Referring now to FIGS. 1 and 6, at block 40 the image data is processed by processor 501. Such processing may include converting the negative image scan data into a positive image for display on a video display unit 503 (at optional block 45); converting the negative image scan data into CNC or other format of output for use by a fabrication device 507 (also known as a prototyping apparatus)(at optional block 50); storing the negative image scan data in a memory location or device 504 (at optional block 55); and/or transmitting the negative image scan data to a remote processor 505 via modem block 502 (at optional block 58).

In the preferred embodiment, one commercially available software package which may be used to generate three dimensional images from the line scan data is the package sold under the designation DataSculpt software available from Laser Design Inc. of Minneapolis, Minn.

Turning now to FIGS. 2a and 2b, the lower impression tray 200 and upper impression tray 220 are illustrated. The trays 200 and 220 are shown without impression material located thereon in order to more clearly illustrate the size and configuration of the respective trays. The trays 200 and 220 are generally horseshoe shaped with an elongate member 204 and 224 (respectively) integrally attached to and extending away from the arcuate portion of the horseshoe section. The elongate members 204 and 224 are generally within the same mean plane formed by the horseshoe section. However, those of skill in the art will appreciate that other locations and arrangements may be utilized. The upper tray 220 also includes a domed element 225 which is integrally formed and connects the interior portion of the horseshoe section of the tray 220.

Each of the trays 200 and 220 also includes a first end 201 and 221 (respectively) which is inserted into a patient's oral cavity during the process of taking the impression and a second end 202 and 222 (respectively) which includes a handle for helping insert and remove the trays. Located proximate the second ends 202 and 222 are holes 203 and 223 (respectively) which are arranged and configured to aid in the registration process of the scanning procedure (i.e., the holes 203 and 223 on the handles may be used in conjunction with the mounting fixture 600). However, including such holes 203 and 223 and/or using the holes in the registration process is optional.

Slots 206 and 226 are formed in the lower and upper trays 200 and 220 (respectively) to aid in the expansion of the impression material when a patient bites into the same, as well as helping retain the impression material on the tray 220 and 226 (and in a fixed manner) after removal from a patient's mouth and during scanning. Only several of the plurality of slots 206 and 226 are designated by the reference numerals in the Figures for the purpose of clarity. Also, those of skill in the art will appreciate that the number and arrangement of the slots 206 and 226 may be changed, with the slots 206 and 226 shown in FIGS. 2a and 2b being illustrative.

The trays 200 and 226 are preferably constructed by means of plastic injection molding process and of a material suitable for medical and dental purposes. Such material should also be selected to be rigid enough to hold the impression material in a stable fashion during scanning and be capable of being sanitized or sterilized.

Turning now to FIGS. 3a and 3b, the bite registration tray 300 is illustrated. Tray 300 is shown without impression material located thereon in order to more clearly illustrate the size and configuration of the tray. The tray 300 is generally horseshoe shaped with an elongate member 304 integrally attached to and extending away from the arcuate portion of the horseshoe section generally in the same mean plane formed by the horseshoe section,.

Tray 300 includes a first end 301 which is inserted into a patient's oral cavity during the process of taking the impression and a second end 302 which includes a handle for helping insert and remove the tray 300. Located proximate the second end 302 is hole 303 which is arranged and configured to aid in the registration process of the scanning procedure (i.e., the hole in the handle may be used in conjunction with the mounting fixture 600). However, including such hole 303 and/or using the hole in the registration process is optional.

FIG. 3b illustrates the bite tray 300 without the elongate member 304 and including an impression retaining mesh material 306 generally located within the horseshoe section. The material 306 is used to retain the impression material on the tray. It will be appreciated that this configuration allows a patient to bite into the impression material on either side of the mean plane formed by the horseshoe portion of tray 300 to register the upper and lower impressions relative to one another so that study casts, visual displays, etc. can be created with the proper spatial relationships. In the preferred embodiment, tray 300 is constructed in a manner similar to that described above in connection with trays 200 and 220.

Related application titled "Buccal Impression Registration Apparatus, and Method of Use", commonly owned by the Assignee of the present invention, describes an apparatus and method for forming a dental impression in order to record the bite registration of a patient's teeth. Such application is incorporated herein by reference and made a part hereof.

Figure 4:
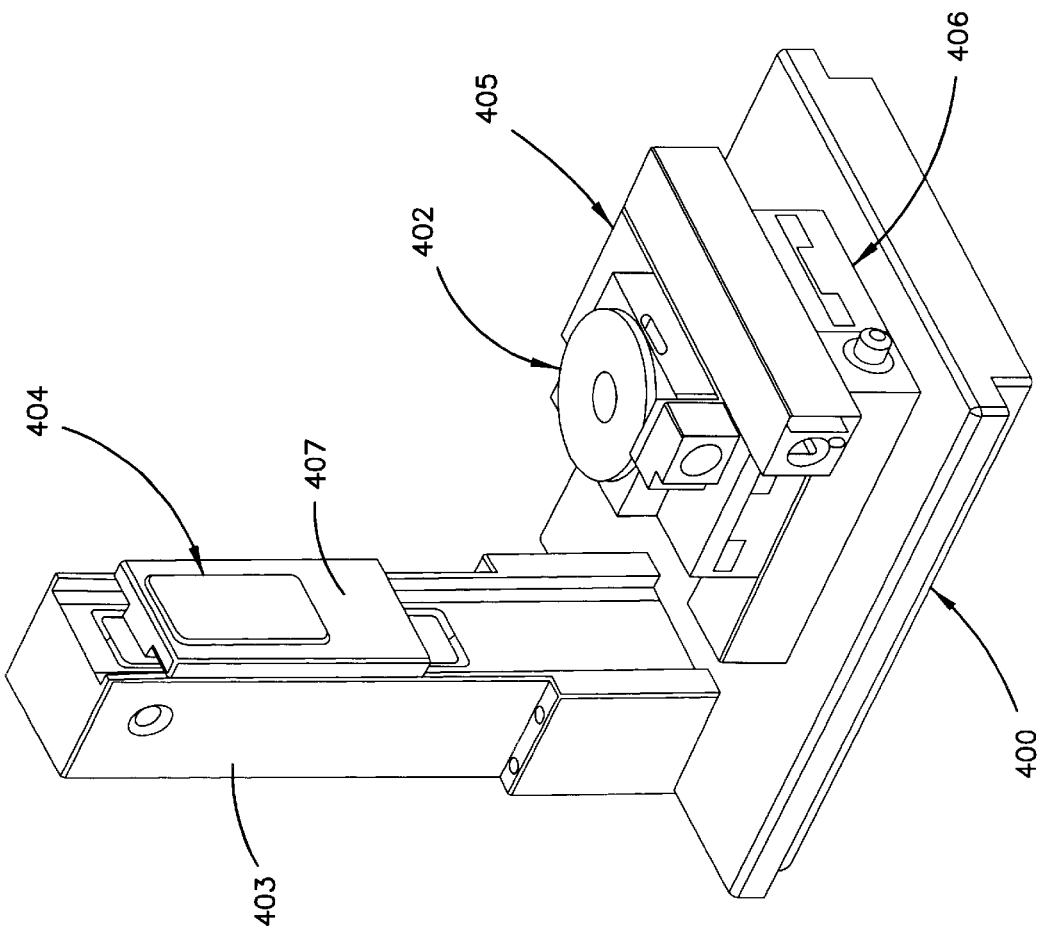
FIG. 4 illustrates a perspective view of a preferred embodiment base 400 and X-Y-Z axis devices 401 used in connection with scanner 60.
Figure 5:
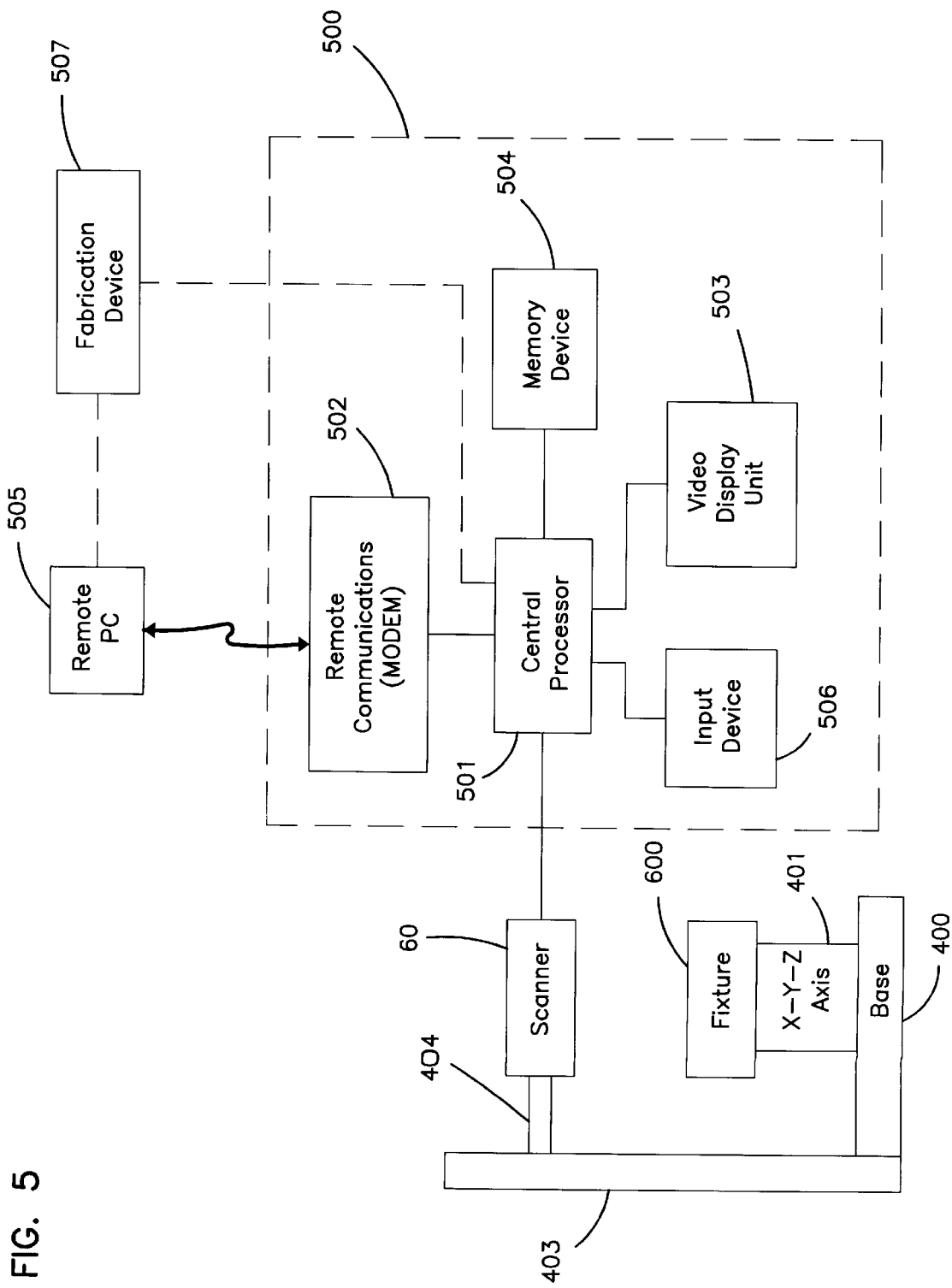
FIG. 5 diagrammatically illustrates the functional blocks associated with the processor, memory, and remote computer associated with processing the data from the scanner 60.

The tooling or fixture 600 is shown as a functional block in FIG. 5. In the preferred embodiment, the fixture 600 is arranged and configured to securely hold the trays 200, 220, and 300 while rotating and/or moving on the stage 402 (best seen in FIG. 4 and described further below) as the array of negative image electronic data from the negative impression (s) is being generated by the scammer 60.

With reference now to FIGS. 7–13, a first embodiment of the fixture or tooling 600 is illustrated. As shown, the fixture 600 is mounted on the stage 402 of the scanning machine, where the table is preferably capable of rotary as well as tilting movements in a manner generally known in scanning machines. The fixture 600 includes a base member 601 mounted on the stage, and a locking fixture 602 detachably connected to the base member 601.

Figure 7:
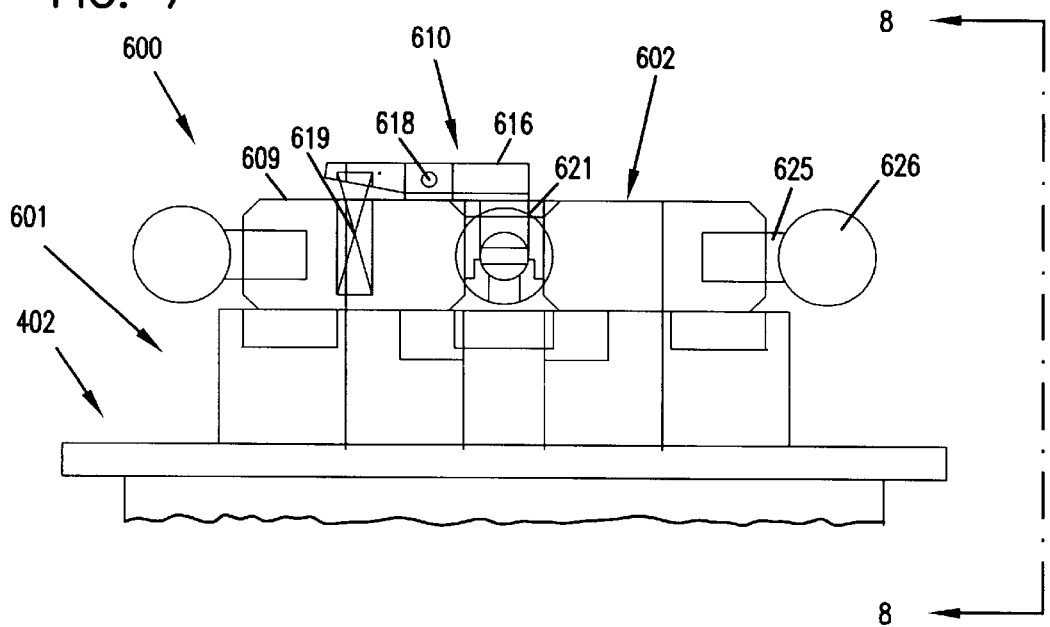
FIG. 7 is a side view of a fixture or tooling for holding an impression tray or study cast on the table of the scanner.
Figure 8:
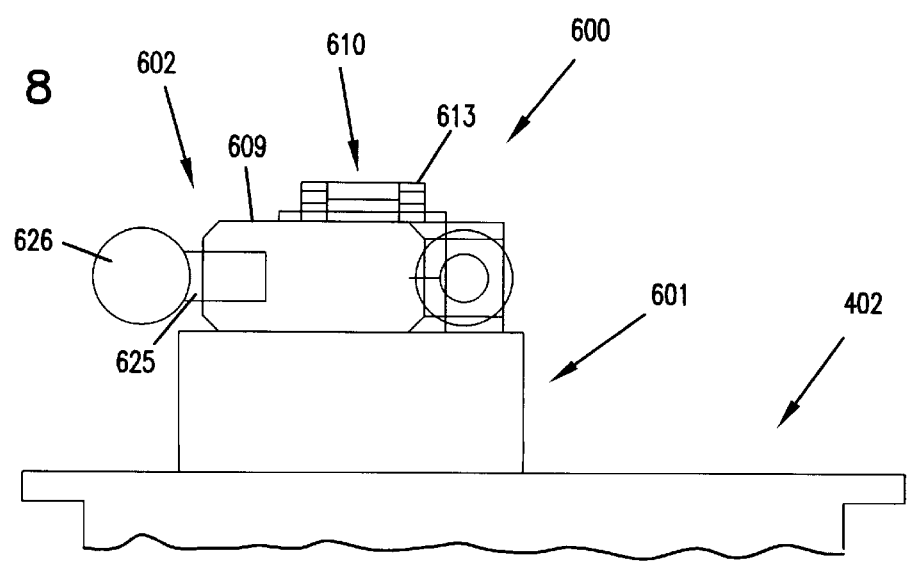
FIG. 8 is a side view looking in the direction of line 8—8 in FIG. 7.
Figure 11:
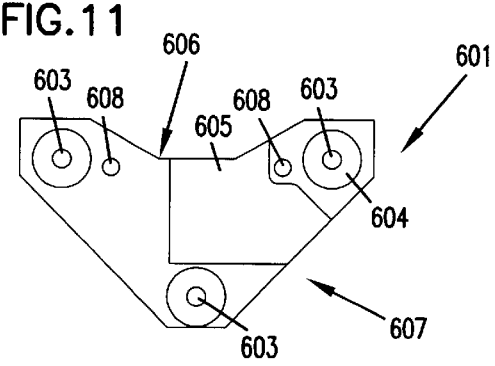
FIG. 11 is a top view of a base member for the tooling.
Figure 12:
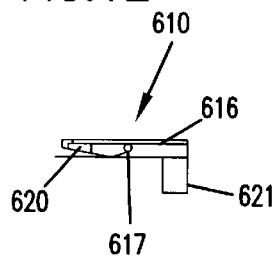
FIG. 12 is a side view of the pivoting lever used with the tooling of FIGS. 7–8.
Figure 13:
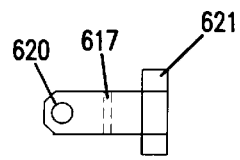
FIG. 13 is a top view of the pivoting lever.

As best seen in FIG. 11, the base member 601 is generally triangular in shape and made from a solid, metal material. Three throughholes 603 are formed in the base member and are aligned with corresponding threaded holes (not shown) in the stage 402. Fasteners (not shown), such as cap screws or the like, are then disposed in the throughholes 603 and threaded into the threaded holes in the stage 402 in order to fasten the base member 601 to the stage. The throughholes are preferably countersunk 604, so that the fasteners do not extend above the top surface of the base member 601, thus permitting the locking fixture 602 to contact the top surface of the base member 601 as shown in FIG. 7. A cut-out section 605 is formed in the base member 601 extending generally from a front 606 of the base member to a rear 607 of the base member. Further, a pair of locating holes 608 are formed in the base member 601 between the cut-out section 605 and a pair of the throughholes 603. The purposes of the cut-out section 605 and the locating holes 608 will become apparent later in the description.

The locking fixture 602 has the same overall shape as the base member and in the preferred embodiment is made from the same metal material. It will be appreciated that other materials might be selected which provide the necessary rigidity and strength to properly secure the trays during scanning. The locking fixture 602 includes a body portion 609 and a clamp means 610 disposed on the body portion for clamping one of the trays 200, 220, and 300 on the body portion to securely hold the tray during the scanning process.

Figure 9:
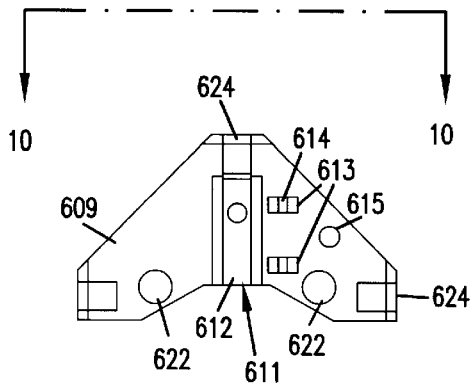
FIG. 9 is a top view of a locking fixture for the tooling in FIGS. 7 and 8.
Figure 10:
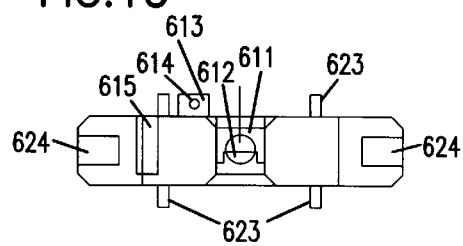
FIG. 10 is a side view looking in the direction of line 10—10 in FIG. 9.

With reference now to FIGS. 9 and 10, the details of the body portion 609 are illustrated. The body portion 609 includes a lowered channel area with side walls defining a groove 611. The groove 611 extends from a front of the body portion toward the rear thereof, but in the preferred embodiment stops short of the rear. The groove 611 is sized so as to receive the elongate handle members 204, 224, and 304 of the trays therein. A generally planar surface 612 defines the bottom of the groove 611, and forms a surface against which the elongate handle members are clamped.

A pair of spaced flanges 613 extend upwardly from the top surface of the body portion on one side of the groove. Each flange 613 includes a pivot hole 614 formed therein extending generally parallel to the groove 611. Further, a hole 615 is formed in the body portion through the top surface thereof. The preferred location of the hole 615 is on an imaginary line running perpendicular to the groove 611 and generally midway between the flanges 613. The hole 615 lies on the distal end of the imaginary line relative to the flanges 613. The clamp means 610 includes a lever 616 with a hole 617 located proximate the midpoint thereof. The lever 616 is pivotally connected between the flanges 613 by a pivot shaft 618 extending through the holes 614 and 617. A coil spring 619 is disposed within the hole 615, and an end of the spring is disposed within a recess 620 provided in the end of the lever to bias the lever in a clamping direction. The opposite end of the lever includes a clamp block 621 connected thereto which extends into the groove 611 and is generally parallel therewith to engage with the handle members of the trays.

As will now be apparent to those of ordinary skill in the art, a tray is clamped by the locking fixture 602 by the following steps. First, a downward force is applied on the end of the lever against the bias of the spring so as to raise the clamp block. Second, the handle member of the tray is then fully inserted into the groove between the clamp block and the planar surface 612. Third, the lever is then released, with the spring biasing the clamp block into engagement with the handle member, thus clamping the handle member between the clamp block and the planar surface. The tray is thus securely fixed for subsequent scanning by the scanner 60.

It is to be realized that the groove 611, surface 612 and surrounding structure could have other shapes and configurations so as to accommodate any type of impression tray handle. For instance, if the impression tray handle were completely flat, the surface 612 could be modified so that the bottom of the groove 611 is completely flat to match the flat impression tray handle.

The biasing force of the spring should be sufficient to maintain a clamping force that is able to hold the weight of the tray and the impression material thereon. The fixture could also be used to hold a study cast for scanning by the scanner. The study cast would be provided with a handle member similar to the handle members 204,224 to permit the study cast to be clamped on the fixture 600.

As described above with reference to FIGS. 2a and 2b, separate trays 200,220 are used to generate an impression of the upper and lower sets of teeth. However, a two-sided impression tray could be used to simultaneously generate an impression of the upper and lower teeth. The two-sided impression tray would have a handle similar to the handles 204, 224. The two-sided impression tray may be secured to the fixture in the same manner as described above. However, once the tray is secured to the fixture and scanning commences, it is not desirable to move the tray relative to the fixture (e.g., since this may affect the results of the scanning). Therefore, since the scanner scans only one side of the two-sided impression tray at a time, the other side of the tray must be able to be positioned for scanning by the scanner, without removing the tray from the fixture.

The fixture 600 of the present invention is designed so as to accommodate such a two-sided impression tray. As shown in FIGS. 9 and 10, the body portion 609 includes a pair of holes 622 therein disposed on each side of the groove adjacent the front of the body portion, at corresponding locations to the locating holes 608 in the base member. A pair of locating pins 623 are suitably mounted in the holes 622 and extend past the top and bottom surfaces of the body portion. The pins 623 thus detachably connect the locking fixture 602 to the base member 601. In use, the two-sided tray is secured to the fixture in the manner previously described, with the fixture oriented as shown in FIG. 7. The upper impression formed on the tray is then scanned. In order to scan the lower impression, the locking fixture 602 is lifted upward until the pins that extend from the bottom of the fixture are disengaged from the locating holes 608. The locking fixture 602 is then "flipped over" and re-secured to the base member by inserting the pins that extend from the top of the fixture 602 into the locating holes. The cut-out section 605 in the base member accommodates the flanges 613 and lever 616 when the locking fixture is flipped over to permit the top surface of the body portion to contact the top surface of the base member. Scanning of the lower impression can then commence. Thus it can be seen that the location and orientation of the two-sided tray on the fixture 600 is not altered, thus improving the results of the scanning of both impressions.

The body portion 609 also includes a plurality of holes 624 therein that receive pins 625 connected to tooling balls 626. The tooling balls are used for reference purposes by the scanner during initializing of the scanning sequence.

An alternate fixture 600' is illustrated in FIGS. 14–17. The alternative fixture 600' is useful for holding impression trays and study casts that do not include a handle member. The fixture 600' includes a base member 601' of generally the same overall structure as the base member of the first embodiment, as illustrated by dashed lines in FIG. 15, with the base member 601' being secured to the stage 402 in the same manner as the first embodiment. A locking fixture 602' is secured to the base member 601' for clamping the tray or study cast thereon. The base member 601' is preferably identical to the base member 601 to permit interchangeable use of the locking fixtures 602, 602'.

The locking fixture 602' includes a body portion 640 and a clamp means 641 disposed on the body portion for clamping a handleless tray or study cast on the body portion to securely hold the tray or study cast during the scanning process.

Figure 15:
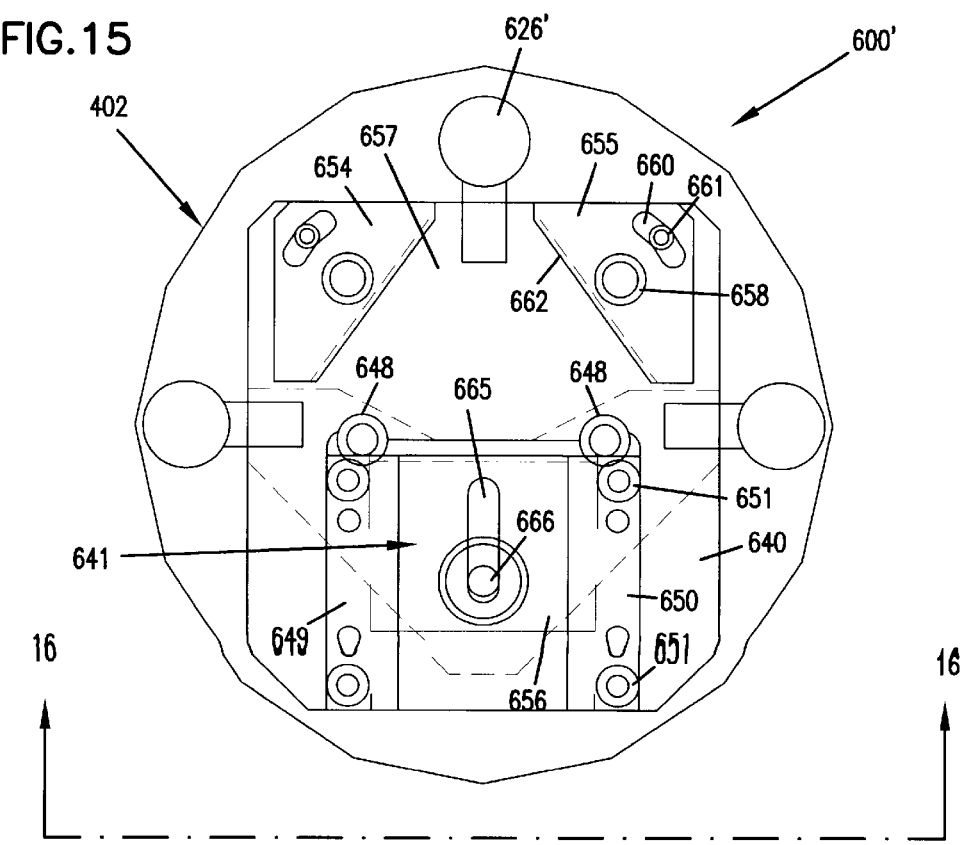
FIG. 15 is a top view of the second fixture or tooling looking in the direction of line 15—15 in FIG. 14.
Figure 17:
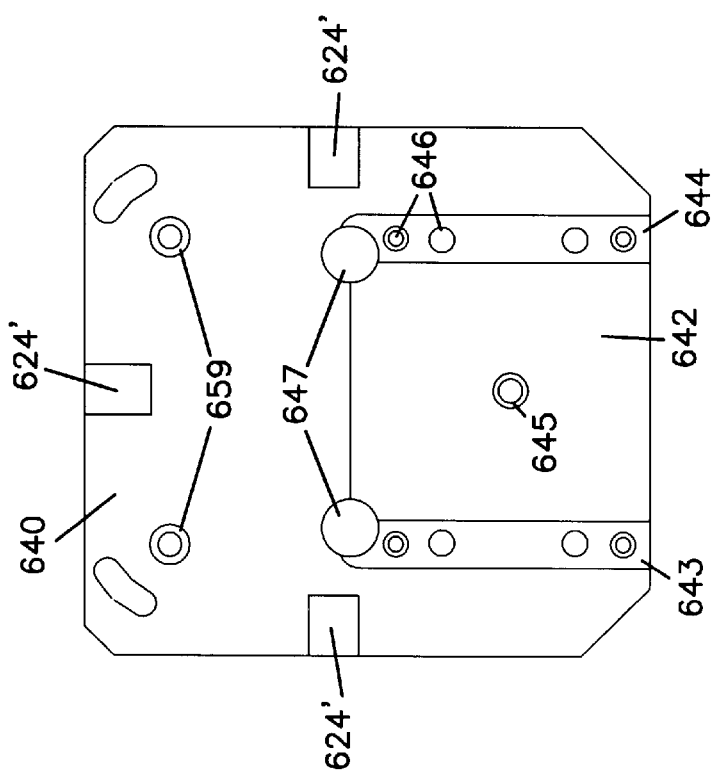
FIG. 17 is a top view of a body portion of the fixture or tooling.
Figure 16:
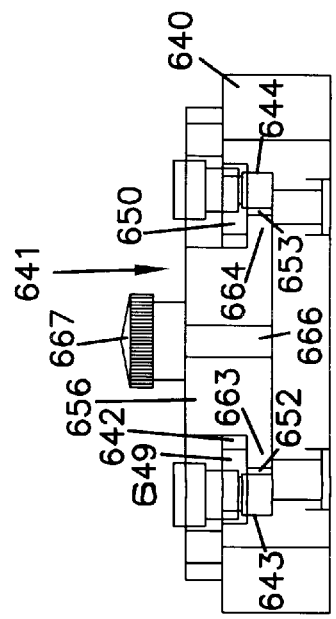
FIG. 16 is a side view looking generally in the direction of line 16—16 in FIG. 15.

With reference to FIGS. 15–17, it can be seen that the body portion 640 is generally rectangular in shape and includes a recessed central portion 642 with a pair of raised shoulders 643, 644 extending along each side of the recessed portion. An internally threaded hole 645 is formed in the center of the recessed portion 642, and a series of threaded holes 646 are formed in each raised shoulder 643, 644. Further, a pair of holes 647 are formed through the body portion 640 at the ends of the shoulders 643,644 at locations corresponding to the locating holes 608 in the base member 601', to permit attachment of the body portion to the base member using fasteners 648, such as cap screws or the like, by inserting the fasteners through the holes 647 and into threaded engagement with the locating holes 608.

A pair of rectangular bars 649, 650 are fastened to the top surfaces of the shoulders 643, 644 by suitable fasteners 651 extending through the bars and into engagement with the holes 646. The bars 649, 650 have a length generally equal to the length of the shoulders, but are wider than the shoulders so as to overhang the top surface of the recessed portion 642 to thus define a pair of tracks 652, 653 between the overhanging portion of the bars and the surface of the recessed portion.

The clamp means 641 comprises a pair of clamp blocks 654, 655 fixed to the body portion, and a slide block 656 slidably mounted in the recessed portion 642, with a clamp section 657 formed between the blocks 654–656.

Figure 14:
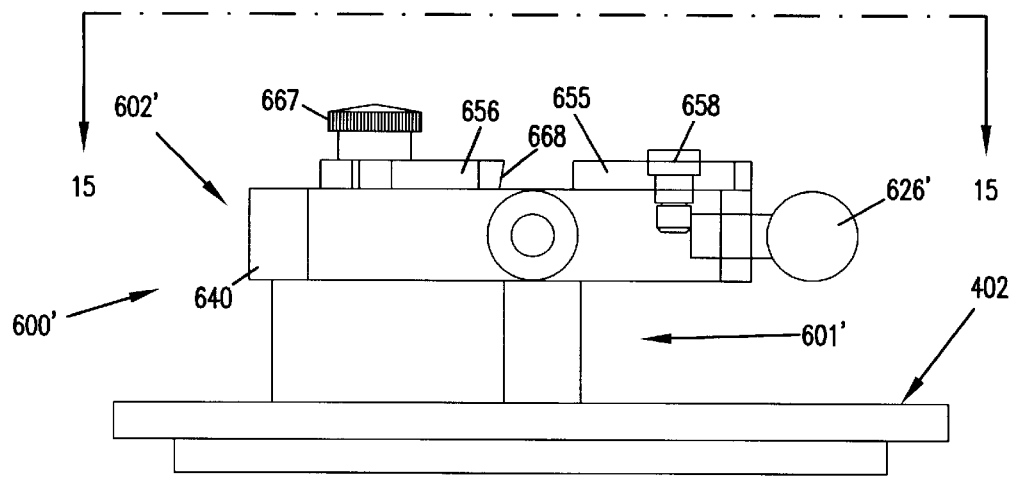
FIG. 14 is a side view of a second embodiment of the fixture or tooling.

As best seen in FIGS. 14 and 15, each clamp block 654, 655 is fastened to the top of the body portion 640 by a fastener 658 which engages with a threaded hole 659 in the body portion. Each clamp block further includes an arcuate slot 660 formed therethrough which receives a pin 661 that is rigidly connected to the body portion in any suitable manner. The angular position of the clamp blocks can be adjusted by loosening the fasteners 658 and pivoting the clamp blocks within the extent permitted by the arcuate slots 660, and then re-tightening the fasteners 658. Further, each clamp block includes a clamping surface 662 that faces toward the clamp section. The clamping surfaces 662 are angled slightly downward relative to a vertical axis (as illustrated by dashed lines in FIG. 15) such that when a tray or cast is clamped in the clamping section 657, a downward force is generated on the tray or cast.

The slide block 656 is a generally rectangular member having a pair of side rails 663, 664 at the bottom thereof that are disposed for sliding movement within the tracks 652, 653. An elongated slot 665 is formed through the slide block generally parallel to the side rails, and a threaded stud 666 is secured within the threaded hole 645 of the recessed portion 642 and extends through the slot 665 beyond the top surface of the slide block. A locking knob 667 is threaded onto the end of the stud for fixing the location of the slide block.

It should be apparent that by loosening the knob 667, the slide block can be slid back and forth within the extent permitted by the slot 665, with the side rails being guided within the tracks. When a dental member, such as a tray or cast, is to be fixed within the clamping section, the member is placed on the clamping section, and the slide block slid forward until it engages the member. The position of the slide block is then fixed by tightening the knob 667. Like the clamping surfaces 662 of the clamp blocks, the slide block includes a clamping surface 668 that faces the clamping section, with the clamping surface being angled downward relative to the vertical direction (as seen in FIG. 14) to provide a downward force on the dental member when clamping occurs.

The body portion 640 is further provided with holes 624' to permit mounting of tooling balls 626', in the same manner as in the first embodiment.

Next, reference should be had to FIGS. 4 and 5 where a more detailed discussion of a scanner, its components and operation will be presented. In FIGS. 4 and 5, the scanner is designated generally at 60. As noted above, the scanner 60 and its operation is described in detail in U.S. Pat. No. 5,124,524. Also shown in FIG. 4 is the Z-axis column 407 which preferably provides precise vertical linear motion with a screw and nut assembly. Scanner mounting member 404 is operatively connected to the Z-axis column 407. Rotary stage 402 preferably provides precise rotational movement in the range of 0.001" quadrature resolution. The stage 402 can also have tilt movements, in addition to its rotary movements. X-axis stage 406 and Y-axis stage 405 provide X and Y coordinate control and preferably use lead screw assemblies. Column 403 is attached to base 400 and supports the scanner 60. In FIG. 5, the X axis stage 406, Y axis stage 405, the Z axis stage 407 and the rotational stage 402 are together referred to as block 401.

Still referring to FIG. 5, the functional blocks of the electronic components of the present invention are illustrated. The components include a computer 500 which preferably includes a processor 501, a video display unit 503, a memory device 504, a user input device 506 (e.g., a mouse and/or keypad), and a modem 502. Also illustrated is a remote computer 505, a fabrication device 507, and the scanner 60 (and its attendant X-Y-Z axis controllers and motors).

It will be appreciated by those of skill in the art that the computer 500 may be a personal computer (e.g., a Pentium based PC) or a special purpose computer. Further, the video display unit 503 may include any number of display devices such as cathode ray tubes, LCD displays, etc. Still further, the memory device 504 may include hard drives, floppy drives, magnetic tape, CD-ROM, random access memory, and read-only memory devices. Further, the modem 502 is illustrated to show a communications capability. Such capability may also be by way of a network, etc.

Fabrication device 507 may be connected directly to the computer 500 or may be connected to a remote computer 505. The fabrication device 507 may be any number of devices which can utilize computer generated data and create a three-dimensional object from such data. One example of such a machine are the devices utilizing stereo lithography technology manufactured by 3-D Systems of Valencia, Calif. under the model designations SLA-250 and SLA-500. Another example is the device utilizing filament technology (fused deposition modeling) manufactured by Statasys Corporation of Minneapolis, Minn. under the model designation FDM-1500.

In operation the array of negative image scan data is generated by the scanner 60 and provided to the processor 501. The negative image scan data may be saved in a memory device 504 as a permanent record of the baseline condition of the patient's teeth, or temporarily prior to one of several other options. For example, the data may be converted to a positive image and stored in that fashion as a permanent record of the baseline condition. Alternatively, the positive image may be displayed on the video display unit 503 for teaching or educational purposes with the patient. Still further, the positive information data may be transmitted to a remote PC 505 for storage, study by a consulting dentist (or physician), or fabrication of a study cast by fabrication device 507. The fabrication device 507 may optionally be connected directly to computer 500. These and other options may be selected by the computer 500 user via the input device 506.

The programming operation of the processor 501 provides for scanning each of the upper and lower impressions and the bite registration impression. These scans provide the information necessary to create an electronic equivalent of the prior art physical study casts. By using negative image impressions and a line scanner, high resolution and speed are gained wherein high quality study casts may be generated by a fabrication device 507 thereby replacing older methods of constructing the same. Although such fabricated casts may still be saved, since the data is generated and stored electronically, the problems associated with storage of prior art study casts may be reduced and/or eliminated. Further, the data may be used any number of times in different ways to accomplish a more robust practice.

It is contemplated that other impressions of a patient's body may be taken to form a negative image mold and subsequently mounted on the fixture for scanning by the scanner.

FIGS. 18–21 illustrate a registration fixture 700 that is used to simultaneously hold study casts of upper and lower sets of teeth while enabling the study casts to be brought into precise registration with each other to reflect the bite registration of the patient. The fixture 700 includes a rigid, L-shaped support base 702 made from a metal material, and includes a horizontal plate portion 704 and a vertical plate portion 706 extending vertically from the plate portion 704.

The support base 702 is adapted to be mounted on the base member 601 illustrated in FIGS. 8–13 upon removal of the locking fixture 602. To accomplish such a mounting, the support base 702 includes a pair of threaded cap screws 708 extending through the horizontal plate portion 704 and adapted to extend through a pair of the throughholes 603 formed in the base member 601 and into threaded engagement with the corresponding threaded holes formed in the stage 402. In this manner, the support base 702 is secured to the base member 601, with both the base member 601 and support base 702 being secured to the stage 402. A pair of cylindrical stand-offs 710 are connected to the bottom of the plate portion 704 to space the fixture 700 from the stage 402 as well as to help stabilize the fixture 700.

A left, or first, locking fixture 712 is secured to the vertical plate portion 706 and extends generally parallel thereto. The construction of the locking fixture 712 is generally identical to the locking fixture 602' in FIGS. 14–17, and thus includes a body portion associated therewith, as well as clamp mechanism, similar to the body portion 640 and clamp means 641 of the locking fixture 602'. Since the details of the locking fixture are completely described in relation to FIGS. 14–17, the details of the locking fixture 712 are not shown in FIGS. 18–21. The locking fixture 712 is intended to securely hold one of the study casts of the upper and lower sets of teeth, preferably the study cast for the lower set of teeth, on the fixture 700. However, it is to be realized that the locking fixture 712 could hold the study cast of the upper set of teeth if desired.

Figure 18:
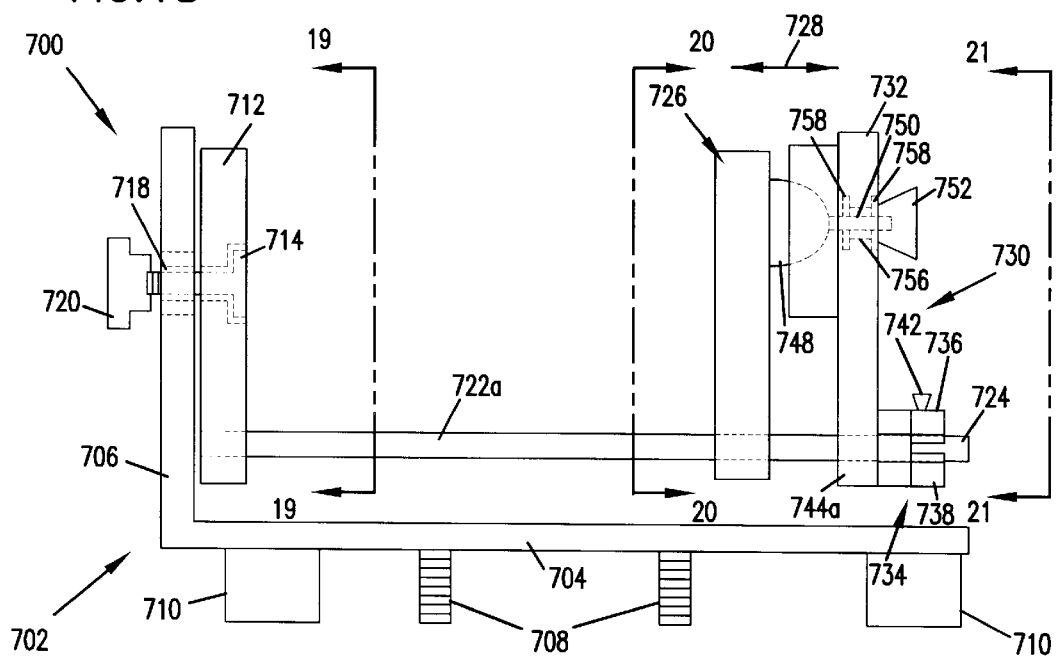
FIG. 18 is a side view of a registration fixture in accordance with the present invention.
Figure 19:
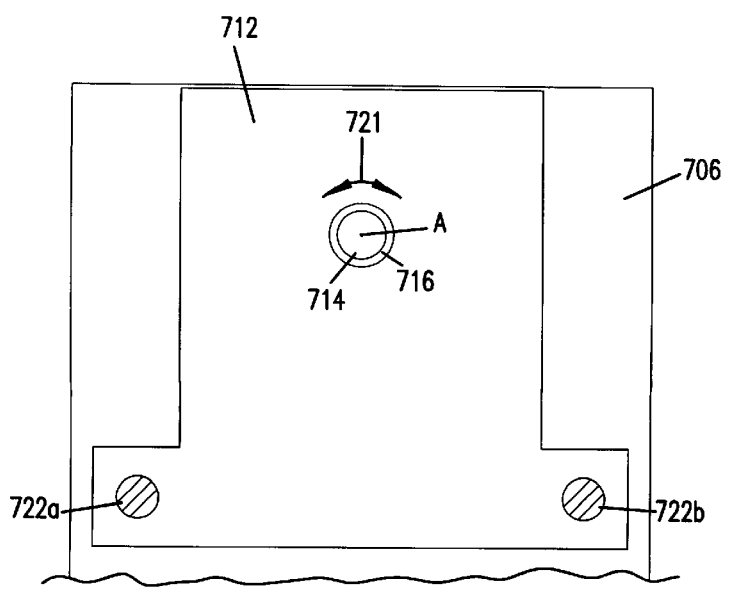
FIG. 19 is a sectional view taken along line 19—19 of FIG. 18 illustrating the left hand locking fixture.

With reference to FIGS. 18 and 19, it is seen that the locking fixture 712 is secured to the plate portion 706 via a cap screw 714 (illustrated in dashed lines in FIG. 18) that extends through a countersunk hole 716 provided in the locking fixture 712 and through a hole 718 provided in the plate portion 706. The cap screw 714 is threaded at one end and an adjustment knob 720 threads onto the threaded end of the cap screw. The intermediate portion of the cap screw 714 is unthreaded and forms a bearing about which the locking fixture 712 is able to pivot when the knob 720 is loosened, whereby the locking fixture 712 is pivotable back and forth about the axis A defined by the cap screw 714 and extending perpendicular to the plane of FIG. 19 as shown by the arrow 721 therein. Thus, by loosening the knob 720, the angular orientation of the locking fixture 712, and the study cast held thereby, can be adjusted as desired. Once the desired angular orientation is achieved, the locking fixture 712 is then fixed in that orientation by tightening the knob 720 which clamps the locking fixture 712 to the plate portion 706 and prevents further movement of the fixture 712.

A pair of elongate, cylindrical guide rods 722a, 722b are fixed to the locking fixture 712 adjacent the bottom thereof, such that the guide rods 722a, 722b pivot with the fixture 712. The guide rods 722a, 722b are substantially parallel to each other, with one end of each rod 722a, 722b being fixed to the fixture 712, and a second, distal end 724 of each guide rod being spaced from the fixture 712. The guide rods 722a, 722b each have substantially smooth, low friction outer surfaces for a purpose which will become apparent later in the description.

A right, or second, locking fixture 726 is provided on the registration fixture 700. Like the first locking fixture 712, the construction of the locking fixture 726 is generally identical to the locking fixture 602' in FIGS. 14–17, and thus includes a body portion associated therewith, as well as clamp mechanism, similar to the body portion 640 and clamp means 641 of the locking fixture 602'. Since the details of the locking fixture are completely described in relation to FIGS. 14–17, the details of the locking fixture 726 are not shown in FIGS. 18–21. The locking fixture 726 is intended to securely hold one of the study casts of the upper and lower sets of teeth, preferably the study cast for the upper set of teeth, on the fixture 700. Of course, it is to be realized that the locking fixture 726 could hold the study cast for the lower set of teeth.

The second locking fixture 726 is mounted on the fixture 700 so as to be moveable toward and away from the first locking fixture 712, as shown by the arrow 728 in FIG. 18, so that the study cast held by the locking fixture 726 can be brought toward the study cast held by the locking fixture 712, so that the bite registration of the patient can be viewed. The second locking fixture 726 is also mounted on the fixture 700 so that it is adjustable relative to the first locking fixture 712, thereby enabling precise registration between the study casts.

Figure 20:
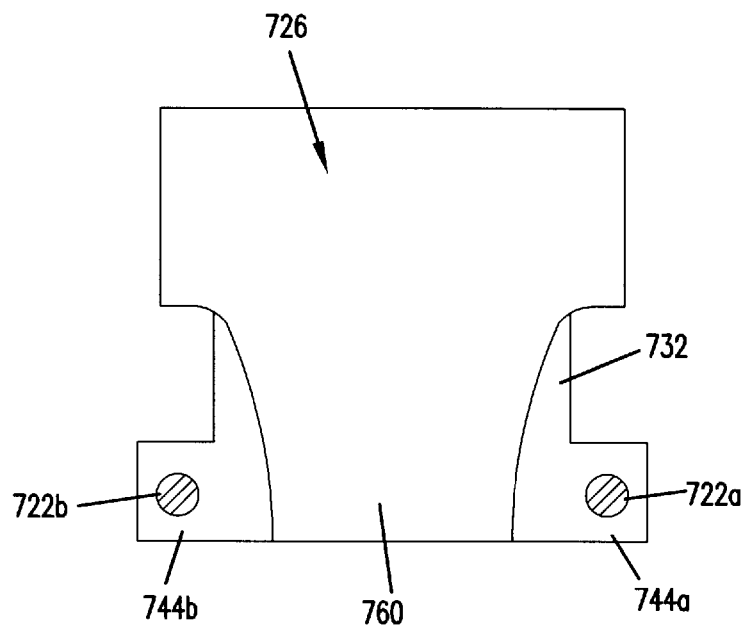
FIG. 20 is a sectional view taken along line 20—20 of FIG. 18 illustrating the right hand locking fixture.
Figure 21:
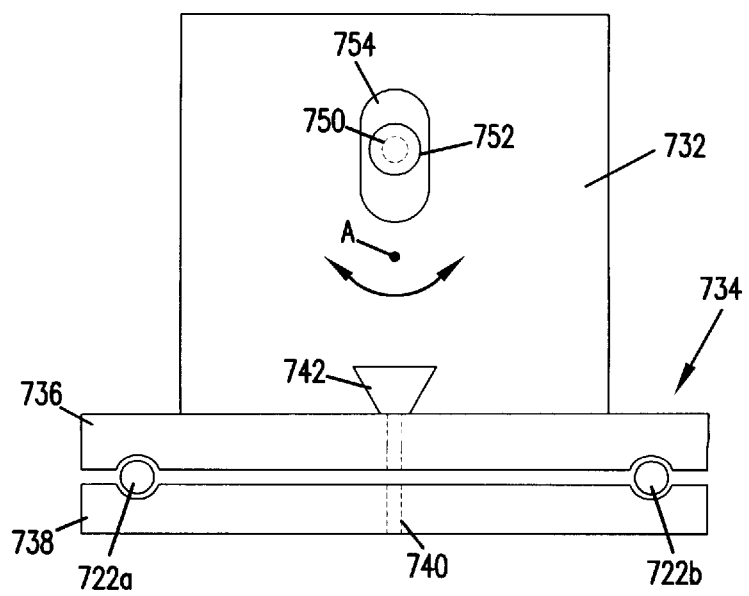
FIG. 21 is an end view taken along line 21—21 of FIG. 18 illustrating details of the guide rod clamp.

With reference to FIGS. 18 and 20–21, the details for mounting the locking fixture 726 for movements in the direction of the arrow 728 are shown in detail. A guide rod clamp 730 having a vertically oriented plate 732 is provided adjacent the locking fixture 726, with the plate 732 oriented generally parallel to the fixture 726. A clamp mechanism 734 is disposed at the base of the plate 732 for sliding engagement with the guide rods 722a, 722b. The clamp mechanism 734 includes an upper clamp portion 736 and a lower clamp portion 738 which together define a pair of channels for receiving the guide rods 722a, 722b. A threaded screw 740 extends upwardly from the lower clamp portion 738 and through the upper clamp portion 736, and an adjustment knob 742 is threaded onto the end of the screw 740.

It should be evident that by rotating the knob 742 in one direction, the clamping portions 736, 738 are drawn together, thereby clamping the guide rods 722a, 722b between the clamp mechanism 734 and preventing sliding movement of the guide rod clamp 730 along the guide rods 722a, 722b. By rotating the knob 742 in the opposite direction, the clamping portions 736, 738 are loosened, thereby permitting the guide rod clamp 730 to freely slide along the guide rods 722a, 722b either towards or away from the first locking fixture 712 to a desired position where the guide rod clamp is subsequently fixed in position by rotating the knob in the tightening direction.

As evident from FIG. 18, the clamp mechanism 734 projects horizontally from the plate 732 to provide sufficient space for the knob 742 and actuation thereof. A pair of ears 744a, 744b are formed at the bottom edge of the plate 732, with the ears 744a, 744b thus being horizontally spaced from the upper and lower clamp portions 736, 738, whereby the guide rods 722a, 722b extend through the ears 744a, 744b as well as through the clamp portions 736, 738.

A block 746 is securely fixed to the face of the plate 732 that faces the first locking fixture 712. The block 746 is formed with a socket (not visible in the figures) that receives therein a substantially hemispherical ball 748 fixed on the back side of the second locking fixture 726. The ball 748 and corresponding socket in the block 746 thus form a ball joint by which the second locking fixture 726 is able to be adjusted relative to the guide rod clamp 730, and thus relative to the first locking fixture 712. Projecting from the end of the ball 748 is a threaded member 750 which extends through the plate 732, and a knob 752 is screwed onto the end of the member 750 for selectively fixing the position of the locking fixture 726.

As illustrated in FIG. 21, the plate 732 is provided with a slot 754 that is elongated vertically, as well as having a horizontal dimension that is greater than the diameter of the threaded member 750. The relatively large size of the slot 754 accommodates movement of the threaded member 750 as the second locking fixture 726 is pivoted. To enable clamping and fixing of the second locking fixture 726, as well as to provide a slight resistance to movement of the fixture 726 when the knob 752 is loosened, a coil spring 756 is disposed around the threaded member 750 between two washers 758.

It should be apparent that by rotating the knob 752 in one direction, the locking fixture 726 is clamped to the plate 732 and thereby fixed in position relative to the plate 732. By rotating the knob in the opposite direction, such as when adjustment of the orientation of the locking fixture 726 is desired, the locking fixture 726 is able to be adjusted to the desired orientation due to the movements permitted by the ball 748 and socket joint, with the coil spring 756 provided a certain resistance to the movement of the locking fixture 726. Once the locking fixture 726 has been suitably oriented, the knob 752 is once again tightened to fix the orientation of the fixture 726 and the study cast held thereby.

It is to be noted from FIG. 20 that the bottom edge 760 of the locking fixture 726 is suitably shaped such that the bottom edge 760 is disposed between the two guide rods 722a, 722b, so that the locking fixture 726 can pivot without interference from the guide rods 722a, 722b. It should be further apparent from FIGS. 18–21 that the second locking fixture 726 and the guide rod clamp 730 pivot simultaneously with the pivoting movements of the first locking fixture 712 about the axis A, since the guide rod clamp 730 is disposed on the guide rods 722a, 722b, and the second locking fixture 726 is connected to the guide rod clamp 730. In this manner, each of the study casts that are held by the locking fixtures 712, 726 can be simultaneously adjusted relative to the support base 702. Further, as described above, the orientation of the second locking fixture 726 can be adjusted independently of the first locking fixture 712, to enable precise registration between the study casts to be achieved.

In use of the registration fixture 700, the study cast of the lower set of teeth is mounted onto the first locking fixture 712, and the study cast of the upper set of teeth is mounted onto the second locking fixture 726. The clamp mechanism 734 is then loosened by loosening the knob 742, and the assembly formed by the guide rod clamp 730 and locking fixture 726 is slid along the guide rods 722a, 722b to bring the study cast of the upper set of teeth close to the study cast of the lower set of teeth held by the locking fixture 712. In the event of slight misalignment between the two study casts, the knob 752 is loosened, thereby allowing the locking fixture 726 to be pivoted so as to bring the study casts into precise registration. Once the correct registration is achieved, the knobs 742, 752 are tightened, thereby fixing the position of the locking fixture 726. To permit observation and analysis of the registered study casts from different orientations, the knob 720 is loosened, thereby enabling the assembly formed by the locking fixture 712, guide rods 722a, 722b, guide rod clamp 730 and locking fixture 726 to pivot about the axis A of the cap screw. Thereafter, the knob 720 is tightened to fix the orientation of the study casts.

While a particular embodiment of the invention has been described, it will be understood that by those skilled in the art that the invention is not limited by the application, embodiment or the particular devices disclosed and described herein. It will be appreciated that other devices that embody the principles of this invention and other applications therefor other than as described herein can be configured within the spirit and intent of this invention. The system described herein is provided as only one example of an embodiment that incorporates and practices the principles of this invention. Other modifications and alterations are well within the knowledge of those skilled in the art and are to be included within the broad scope of the appended claims.

What is claimed is:

1. A fixture for holding a dental member on a scanning machine during scanning of the dental member by the scanning machine, comprising:

a base member adapted so as to be mountable onto a stage of the scanning machine; and a locking fixture detachably connected to the base member, said locking fixture including a body portion and a clamp means disposed on the body portion for clamping the dental member on the locking fixture;

wherein said body portion includes a groove formed therein with a planar surface defining a bottom of the groove, and said clamp means clamps at least a portion of the dental member within the groove against the planar surface; and wherein said clamp means comprises a lever pivotally attached to the body portion, said lever includes a clamp block connected to one end thereof, said clamp block being disposed within said groove and in alignment with said planar surface to thereby clamp the dental member portion between the clamp block and the planar surface.

2. The fixture according to claim 1, wherein said lever is pivoted about an axis that extends generally parallel to said groove.

3. The fixture according to claim 1, further including means for biasing the lever and the clamp block toward the planar surface.

4. The fixture according to claim 3, wherein said means for biasing comprises a spring, said spring being disposed on said body portion and engaged against an end of said lever opposite said one end.

5. The fixture according to claim 1, further including a pair of upright, spaced flanges connected to said body portion, said lever being pivotally connected to said flanges and disposed therebetween.

6. The fixture according to claim 5, wherein said base member includes a cut-out section formed therein, said cut-out section being sized and located on said base member so as to receive said flanges and said lever.

7. The fixture according to claim 1, wherein said body portion includes upper and lower surfaces, and a pair of locating pins connected to said body portion and projecting above said upper and lower surfaces, said base member including a pair of locating holes formed therein at locations corresponding to said locating pins, said locating pins being disposed within said locating holes to thereby detachably connect said body portion to said base member.

8. A fixture for holding a dental member on a scanning machine during scanning of the dental member by the scanning machine, comprising:

a base member adapted so as to be mountable onto a stage of the scanning machine;

a locking fixture detachably connected to the base member, said locking fixture including a body portion and a clamp means disposed on the body portion clamping the dental member on the locking fixture;

wherein said clamp means includes a pair of clamp blocks connected to said body portion and a slide block mounted on said body portion for sliding movement relative thereto, said clamp blocks and said slide block forming a clamp section therebetween that is sized so as to receive the dental member; and further including a pair of spaced tracks formed on said body portion, and said slide block includes a pair of rails that are slidably disposed within said tracks.

9. The fixture according to claim 8, wherein said slide block includes a slot formed therethrough extending parallel to said tracks, and further including a stud extending upward from said body portion and through said slot, whereby said slide block is moveable between the ends of said slot.

10. The fixture according to claim 9, further including a locking knob secured to said stud to fix the position of said slide block.

11. The fixture according to claim 8, wherein said clamp blocks and said slide block include clamp surfaces that are angled relative to a vertical axis.

12. A registration fixture, comprising:

a support base;

a first locking fixture secured to the support base, said first locking fixture including a first clamp mechanism configured to clamp a study cast of an upper or lower set of teeth, and wherein said first locking fixture is pivotally secured to said support base, whereby said first locking fixture is pivotable relative to said support base;

a pair of guide rods oriented substantially parallel to each other, each said guide rod including a first end secured to said first locking fixture and a second, distal end spaced from said first locking fixture; and a second locking fixture slidably supported on said guide rods for sliding movement towards and away from said first locking fixture, said second locking fixture including a second clamp mechanism configured to clamp a study cast of an upper or lower set of teeth;

and further including a guide rod clamp slidably disposed on said guide rods and in selective clamping engagement therewith whereby the position of said guide rod clamp along the guide rods is adjustable, and said second locking fixture is connected to said guide rod clamp by a ball joint whereby said second locking fixture is pivotable relative to said guide rod clamp.

13. The registration fixture according to claim 12, wherein said second locking fixture is pivotable relative to said first locking fixture.

* * * * *

UNITED STATES PATENT AND TRADEMARK OFFICE
CERTIFICATE OF CORRECTION

| | | |
|---|---|---|
| PATENT NO. | : 6,200,135 B1 | Page 1 of 1 |
| APPLICATION NO. | : 09/312417 | |
| DATED | : March 13, 2001 | |
| INVENTOR(S) | : Hultgren | |

It is certified that error appears in the above-identified patent and that said Letters Patent is hereby corrected as shown below:

Title Page, Item (63), Related U.S. Application Data: "Jan. 28, 1997, now abandoned." should read --Jan. 28, 1997, now U.S. Patent No. 6,217,334.--

Col. 1, line 7: "Jan. 28, 1997, now abandoned." should read --Jan. 28, 1997, now U.S. Patent No. 6,217,334.--

Col. 1, line 10: "filed on May 14, 2000, and" should read --filed on May 14, 1999, and--

Signed and Sealed this

Twentieth Day of September, 2011

David J. Kappos
*Director of the United States Patent and Trademark Office*